Figure 1:
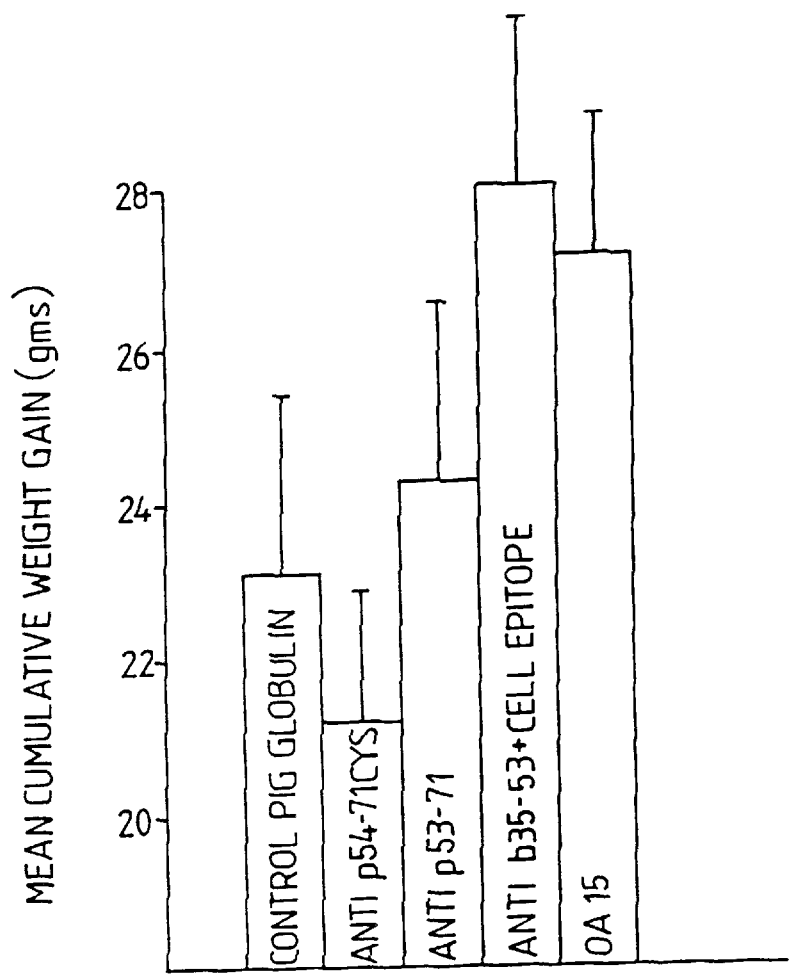

United States Patent [19]

James et al.

[11] Patent Number: 5,864,008
[45] Date of Patent: Jan. 26, 1999

[54] PEPTIDES DERIVED FROM FOOT-AND-MOUTH DISEASE VIRUS, PHARMACEUTICAL COMPOSITIONS, AND METHODS FOR USING THE PEPTIDES

[76] Inventors: Stephen James, Berkhamsted Hill, Berkhamsted, Herts.; David John Rowlands; Michael James Francis, both of Langley Court, Beckenham, Kent, all of England

[21] Appl. No.: 921,447

[22] Filed: Jul. 28, 1992

Related U.S. Application Data

[63] Continuation of Ser. No. 571,615, Nov. 9, 1990, abandoned.

[30] Foreign Application Priority Data

Mar. 25, 1988 [EP] European Pat. Off. ............. 88302656
Sep. 8, 1988 [GB] United Kingdom ................... 8821076

[51] Int. Cl.$^6$ ......................... C07K 14/09; A61K 39/135
[52] U.S. Cl. ......................... 530/324; 530/325; 530/326; 530/327; 530/328; 530/329; 530/330; 530/350; 530/806; 530/826; 424/186.1
[58] Field of Search ..................................... 530/324, 325, 530/326, 327, 328, 329, 330, 350, 806, 826; 424/88, 89, 186.1

[56] References Cited

U.S. PATENT DOCUMENTS 4,544,500 10/1985 Bittle et al. .............................. 930/222
4,558,033 12/1985 Rudman ....................................... 514/4
4,591,552 5/1986 Neurath ....................................... 435/7
4,605,512 8/1986 Schaller et al. .......................... 930/222
4,732,971 3/1988 Dimarchi et al. ....................... 930/222
4,743,554 5/1988 Boothroyd et al. ..................... 930/222

FOREIGN PATENT DOCUMENTS 0 137 904 A3  4/1985  European Pat. Off. .
0 284 406 A1  9/1988  European Pat. Off. .

OTHER PUBLICATIONS

Rudinger, Peptide Hormones, Parsons (Ed.) U Park Press, Baltimore, pp. 1–7 (1976).
Surovoi et al., Bioorg. Khim. 14(10), pp. 1352–1362 (Chem. Abstr. CA110, No. 93126y) 1988.
Francis et al., Nature, vol. 330, pp. 168–170 (Nov. 12, 1987).

*Primary Examiner*—Frank C. Eisenschenk
*Attorney, Agent, or Firm*—Peter F. Corless; Dike, Bronstein, Roberts & Cushman, LLP

[57] ABSTRACT

A peptide and veterinarily acceptable salts thereof are disclosed which comprise an amino acid sequence which is derived from foot-and-mouth disease virus (FMDV). The peptide is independent within the FMDV structure of a B-cell epitope and is capable of eliciting T-cell help in an animal susceptible to FMDV infection for production of antibody against an antigen. Optionally, an amino acid in the sequence may be replaced by another amino acid which does not affect the function of the sequence to elicit T-cell help.

7 Claims, 1 Drawing Sheet

PEPTIDES DERIVED FROM FOOT-AND-MOUTH DISEASE VIRUS, PHARMACEUTICAL COMPOSITIONS, AND METHODS FOR USING THE PEPTIDES

This is a continuation of application(s) Ser. No. 07/571,615 filed on Nov. 9, 1990, abandoned by International Application GB89/00311 filed on Mar. 23, 1989, and which designated the U.S.

This invention relates to synthetic peptides, their preparation and their use as vaccines.

The aims of a good vaccine should be to provide a rapid onset of immunity that is of long duration and provides immunological memory for a subsequent inoculation or encounter with the infectious agent. The vaccine formulation must also be easy to administer, stable, have minimal side effects and produce broad protection in the recipient. These aims are largely met by many existing commercial products. However, conventional vaccines based on inactivated infectious agents do present problems. These include the undefined nature of the immunizing antigen, whether the product is truely innocuous, risk associated with handling large amounts of infectious material, stability and limitations on the mode of presentation, generally resulting from problems of stability.

In an attempt to produce more stable and defined vaccines scientists have been studying the immune response to many infectious agents in detail in order to identify the critical epitopes involved in providing protective immunity. Armed with this knowledge it is now possible to mimic such epitopes by producing short peptides and to use these as the basis of a vaccine. The advantages of such peptide based vaccines are numerous. They are chemically defined, stable indefinitely and no infectious material is involved in their manufacture. Furthermore, they can be designed to stimulate the appropriate immune response and provide the opportunity for using novel delivery systems and for targetting the antigen. From the manufacturers viewpoint they should also reduce the need for a large scale production plant and for complex downstream processing of the product.

Despite these clear advantages a number of criticisms have been levelled at peptide based vaccines. These include the requirements for undefined carrier proteins and the belief that the immunogenicity of a peptide antigen could never approach that of the native organism. It was generally assumed that due to their relatively small molecular size many synthetic peptides would behave like haptens and would require coupling to a large "foreign" protein carrier to enhance their immunogenicity. Immunization with such conjugates often resulted in the production of anti-peptide antibodies that totally failed to recognise the native protein or infectious agent due to the method of peptide/carrier linkage. Other problems, of particular relevance to vaccination, that could be encountered were hypersensitivity to the "foreign" carrier protein and poor batch to batch reproducibility of the conjugates.

We have now located a helper T-cell epitope (a Th-epitope) on foot-and-mouth disease virus (FMDV). This Th-epitope is capable of assisting in the induction of an antibody response to a B-cell epitope in animals susceptible to FMDV infection. This finding has general applicability.

Accordingly, the present invention provides a synthetic peptide presenting an amino acid sequence which is derived from FMDV, which is independent within the FMDV structure of a B-cell epitope and which is capable of eliciting T-cell help in an animal susceptible to FMDV infection for production of antibody against an antigen; and veterinarily acceptable salts thereof. Optionally an amino acid in the sequence may be replaced by another amino acid which does not affect the function of the sequence to elicit T-cell help.

The peptide preferably also presents an amino acid sequence capable of inducing an antibody response to a foreign antigen in an animal susceptible to infection by FMDV (a B-cell epitope). Such peptides comprise a non-natural co-linear sequence of a B-cell epitope and a Th-epitope. The Th-epitope is independent within the FMDV structure of the B-cell epitope. Alternatively, the Th-epitope of the invention and the B-cell epitope may be presented as separate peptides, for example in the same delivery vehicle. Such a delivery vehicle incorporating the two epitopes as separate peptides also forms part of the present invention.

The use of the Th-epitope in association with the B-cell epitope can result in a better antibody response to the B-cell epitope than use of the B-cell epitope alohe. Peptides comprising the Th-epitope and the B-cell epitope, and delivery vehicles comprising the two epitopes as separate peptides, can therefore be used as vaccines. They can also be used to raise antibody to potentiate the activity of a hormone in a vertebrate.

The Th-cell epitope must be capable of binding class II major histocompatibility complex (MHC) molecules on the surface of host antigen presenting cells (APC) and B-cells and of subsequently interacting with the T-cell receptor in the form of a trimolecular complex in order to induce B cells to differentiate and proliferate.

Th-cell epitopes on FMDV may be identified by a detailed analysis, using in vitro T-cell stimulation techniques of component proteins, protein fragments and peptides to identify appropriate sequences (Goodman and Sercarz, Ann. Rev. Immunol., 1, 465, 1983; Berzofsky, in "The Year in Immunology, Vol. 2" page 151, Karger, Basel, 1986; and Livingstone and Fathman, Ann. Rev. Immunol., 5, 477, 1987). Further, there are now two published algorithms that improve the chances of selecting appropriate peptide sequences with T-cell stimulating activity from the primary sequence of a protein.

The first algorithm, proposed by DeLisi and Berzofsky (Proc. Natl. Acad. Sci. USA, 82, 7048, 1985), suggests that T cell sites tend to be amphipathic structures i.e. one portion of the molecule is hydrophobic and the other hydrophilic, which are frequently in the form of an alpha-helix. The originators of this hypothesis have published a computer program (Margalit et al, J. Immunol., 138, 2213, 1987) to assist in the identification of amphipathic helices from the primary amino acid sequence of a protein.

The second algorithm, propose by Rothbard (Ann. Inst. Pasteur, 137E, 518, 1986), suggests that each T-cell epitope has within it a sequence composed of a charged residue or glycine followed by two hydrophobic residues and in many cases the next residue will be charged or polar. This algorithm has been refined to consider further residues flanking the two central hydrophobic amino acids and to suggest possible sub-patterns responsible for the genetic restriction of an epitope (Rothbard and Taylor, EMBO J. 7, 93, 1988).

The Th-epitope is independent within the FMDV structure of a B-cell epitope. In other words, it does not immediately precede or immediately follow the sequence of a B-cell epitope. The Th-epitope is separate from a B-cell epitope within the structure of FMDV. When the B-cell epitope is one from FMDV, the Th-epitope may therefore not be the natural Th-epitope for the B-cell epitope. Preferably the Th-epitope is a bovine, porcine or ovine Th-epitope, i.e. it is a Th-epitope in the context of those animals.

The preferred Th-cell epitope of the invention is derived from the VP3 capsid protein of FMDV. The epitope comprises amino acid residues 173 to 176 of VP3 of FMDV $O_1$ Kaufbeuren or the corresponding amino acids of another strain of FMDV. This may be another strain of $O_1$ or of one of the other serotypes $A_{12}$, $C_3$, Asia 1, SAT 1, SAT 2 or SAT 3. Preferably the epitope comprises VP3 residues 170 to 179 of FMDV $O_1$ Kaufbeuren or the corresponding residues of another FMDV strain. The Th-epitopes derived from $O_1$ Kaufbeuren have the following sequences, using the one letter code:

GVAE (residues 173 to 176) (SEQ ID NO: 1) and
TASGVAETTN (residues 170 to 179) (SEQ ID NO: 2).

The B-cell epitope may be an epitope capable of raising neutralising antibody. The epitope may be a viral epitope, for example the major FMDV epitope. This is typically defined by at least amino acid residues 142 to 160 of the VP1 capsid protein. This applies in particular to FMDV serotype $O_1$. A preferred immunogenic FMDV sequence which may be employed as the B-cell epitope is defined by VP1 amino acid residues 142 to 160 of FMDV serotype $O_1$, optionally extending down to amino acid 137 at the N-terminal and/or up to amino acid 162 at the C-terminal or by corresponding amino acids of another serotype. Typical sequences are VP1 residues 140 to 162, 141–160, 137 to 162 or 137–160, for example of serotype 0 and A such as subtypes $O_1$ and $A_1$.

Smaller immunogenic sequences of the FMDV epitope may be presented, however. For example, the sequence defined by VP1 residues 145 to 150 of serotype $O_1$ may be presented in this way. Consequently the FMDV sequence which can be used as the B-cell epitope may be defined by VP1 residues 145 to 150 of serotype $O_1$, optionally extending down to amino acid 137 at the N-terminal and/or up to amino acid 162 at the C-terminal, or by corresponding amino acids of another serotype.

The B-cell epitope may alternatively be an amino acid sequence of a non-infectious agent such as of a hormone of a vertebrate. More specifically this is a sequence which induces antibody which potentiates the activity of the hormone in the vertebrate. Typically, the sequence is about 25 amino acid residues or less, and more preferably less than 20 amino acid residues.

The number of amino acid residues in the sequence that have structural homology with the hormone is typically dependent upon the length of the sequence and may vary from a few amino acid residues to the entire sequence. Typically, the sequence of amino acid residues having structural homology with the hormone is at least 5 amino acid residues in length and preferably at least about 8 to 10 amino acid residues in length.

As used herein the term "potentiate" means that the sequence, the B-cell epitope, acts directly or indirectly to increase or enhance the activity of the hormone to which it has the structural homology. Accordingly, in one aspect the B-cell epitope is a sequence having primary structural homology to a (preferably continuous) sequence of amino acid residues of bovine growth hormone (GH) in the region spanning positions 35 to 53 thereof or is an antigenically equivalent sequence thereto.

The said region of bovine (and ovine) GH is:
TYIPEGQRYSIQNTQVAFC (SEQ ID NO: 3)

By "primary structural homology" we mean a sequence which precisely duplicates this region; a sequence which duplicates corresponding regions of growth hormone molecules from other species; and other sequences which have minor deletions or conservative substitutions of one or more amino acids such that the tertiary configuaration of the sequence is substantially unchanged.

Examples of substitutions which may be conservative in this context include those having substantially the same hydrophobicity, size, charge and/or aromaticity as the original amino acid residue. All such substitutions and modifications are generally well known to those skilled in the art of peptide chemistry. For example, candidate substitutions include: proline for glycine and vice versa; alanine or valine for glycine and vice versa; isoleucine for leucine and vice versa; tryptophan for tyrosine and vice versa; histidine for lysine and vice versa; serine for asparagine and vice versa; arginine for glutamate and vice versa; threonine for cysteine and vice versa; serine or alanine for threonine and vice versa; and glutamine for asparagine and vice versa.

The following are examples of regions of non-bovine GH's which correspond to the 35–53 region of the bovine growth hormone:

Human 35–53
YIPKEQKYSFLQNPQTSLC (SEQ ID NO: 4)
Porcine and rat 35–53
AYIPEGQRYSIQNAQAAFC (SEQ ID NO: 5)
Avian (35–53)
TYIPEDQRYTNKNSQAAFC (SEQ ID NO: 6)
Salmon (or trout) 31–49
TLLPDERRQLNKIFLLDFC (SEQ ID NO: 7).

The term "antigenically equivalent" means that the sequence can be used, in a suitable formulation, to raise antibodies in a vertebrate, the antibodies acting to potentiate the action of growth hormone in that vertebrate. In particular, sequences which are slightly shorter or longer than the said regions or which overlap substantially with the said regions, for example 30–48 or 26–43, have been found to be antigenically equivalent.

The terms "slightly longer", "slightly shorter" and "substantial overlap" denote sequences in which at least 45% (preferably 50%, 60%, 70%, 80%, 90% or 100%) of the antigenic equivalent sequence overlaps with at least 35% (preferably 40%, 50%, 60%, 70%, 80%, 90% or 100%) of the said 35–53 regions. In particular, antigenically equivalent sequences which are shorter than the said fragments may be used, for example 35–43 or 35–48.

With specific although not exclusive relation to bovine GH, the following sequences are useful: 26–43 (A-Y), 35–43 (T-Y), 37–48 (I-T), 39–46 (E-Q), 43–54 (Y-F) and 43–61 (Y-P).

It has been found that using a sequence from a species other than that of the animal to which a peptide of the invention is to be administered can be advantageous, for example, porcine 35–53 for sheep or cattle. Variations from the sequence of the animal's own GH may cause a greater immune response, whilst still yielding antibodies able to recognise the animal's own GH.

The Th-cell epitope and the B-cell epitope are typically present together in the synthetic peptide. The Th-cell epitope may comprise the amino-terminal portion of the peptide and the B-cell epitope may comprise the carboxy-terminal portion of the peptide, or vice-versa. The peptide may comprise just the two epitopes. Alternatively, the epitopes may form part of a longer peptide. The epitopes may be linked directly together so that one follows immediately after the other. Alternatively, the epitopes may be separated by intervening spacer amino acid residues.

A longer peptide of up to 50, for example of up to 40 or of up to 30, amino acid residues can be built up. Up to four amino acids may be added to either or both ends of the Th-cell epitope and/or of the B-cell epitope, for example. The Th-cell epitope and the B-cell epitope may be spaced apart by up to 10, for example by up to 6 or up to 3, amino acid residues. Further, longer peptides may also comprise more than one Th-cell epitope and/or more than one B-cell epitope. Repeats of an epitope may be present.

If the Th-cell epitope and the B-cell epitope are presented as separate peptides, they may also form part of longer peptides. Such longer peptides may have up to 35, for example up to 20 or up to 10 amino acid residues in total. Amino acid residues may be added to either or both ends of either or both epitopes, for example up to four to the N-terminus and/or up to four to the C-terminus. Preferably the additional amino acids are the natural amino acids which occur alongside the Th-epitope or B-cell epitope in the sequence from which the epitope has been derived.

A cysteine (C) residue may be added to either or both terminals of the peptides. In particular, a C residue may be added to the carboxy-terminus alone. Also, peptides may be provided in which one or more of the amino acid residues are chemically modified, before or after the peptide is synthesised, providing that the function of the peptide, namely the production of specific antibodies in vivo, remains substantially unchanged. Such modifications include forming salts with acids or bases, especially veterinarily acceptable organic or inorganic acids and bases, forming an ester. (such as a $C_1$–$C_4$ alkyl ester) or amide of a terminal carboxyl group, and attaching amino acid protecting groups such as N-t-butoxycarbonyl. Such modifications may protect the peptide from in vivo metabolism.

The peptides are synthetic peptides. They may be prepared by chemical synthesis. A peptide may be built up from single amino acids and/or preformed peptides of two or more amino acids in the order of the sequence of the desired peptide. Solid-phase or solution methods may be employed. The resultant peptide may be converted into a veterinarily acceptable salt if desired.

In solid-phase synthesis, the amino acid sequence of the desired peptide is built up sequentially from the C-terminal amino acid which is bound to an insoluble resin. When the desired peptide has been produced, it is cleaved from the resin. When solution-phase synthesis is employed, the desired peptide may again be built up from the C-terminal amino acid. The carboxy group of this acid remains blocked throughout by a suitable protecting group, which is removed at the end of the synthesis.

Whichever technique, solid-phase or solution-phase, is employed each amino acid added to the reaction system typically has a protected amino group and an activated carboxy group. Functional side-chain groups are protected too. After each step in the synthesis, the amino-protecting group is removed. Side-chain functional groups are generally removed at the end of the synthesis.

The resultant peptide may then be converted into a veterinarily acceptable salt. It may be converted into an acid addition salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

The peptides of the invention may also be prepared by recombinant DNA methodologies. Thus, a DNA sequence encoding the peptide is provided. An expression vector is prepared which incorporates the DNA sequence and which is capable of expressing the peptide when provided in a suitable host. The DNA sequence is located between translation start and stop signals in the vector. Appropriate transcriptional control elements are also provided, in particular a promoter for the DNA sequence and a transcriptional termination site. The DNA sequence is provided in the correct frame such as to enable expression of the peptide to occur in a host compatible with the vector.

Any appropriate host-vector system may be employed. The vector may be a plasmid. In that event, a bacterial or yeast host may be used. Alternatively, the vector may be a viral vector. This may be used to transfect cells of a mammalian cell line in order to cause peptide expression.

In one aspect, the peptides of the invention can be used to raise neutralising antibody. They therefore may be used as vaccines for animals susceptible to infection by FMDV. Vaccination need not necessarily be against FMDV but against any foreign antigen. The invention provides a method of vaccinating an animal susceptible to infection by FMDV against a foreign antigen, which method comprises administering thereto an effective amount of the Th-epitope of the invention and a B-cell epitope capable of inducing antibody against the foreign antigen. Preferably a peptide comprising both epitopes is given.

An oral route or a parenteral route such as subcutaneously, intravenously or intramuscularly may be adopted. Typically, a peptide is administered in an amount of 1 to 1,000 ug per dose, more preferably 10 to 100 ug per dose, by either the oral or the parenteral route.

In another aspect, the invention provides a method of treating a normal or abnormal vertebrate susceptible to FMDV infection with a peptide comprising the Th-epitope of the invention and a B-cell epitope which is an amino acid sequence having primary structural homology to a sequence of amino acid residues of bovine, porcine, ovine or other vertebrate GH in the region spanning positions 35 to 53 thereof or is an antigenically equivalent sequence thereto.

This may be in order, for example, to boost the growth of that vertebrate beyond normal levels or at an accelerated rate, to bring abnormally low levels of growth up to the norm, to boost milk yield or to boost or enhance other biological effects associated with GH. The proportion of lean meat to fat in an animal may also be enhanced by using such methods. The term "vertebrate" includes humans and non-humans.

In this instance, the peptides of the invention will usually be administered intravenously, sub-cutaneously or intramusculary although intranasal, transdermal, oral and rectal routes may be suitable for the some formulatins. The formulation will normally be sterile and (for parenteral use) non-pyrogenic. A unit dose will typically include 1 to 1000 ug of the peptide of the invention, typically 10 to 500 ug, preferbly about 50 ug or less. One or more repeat immunisations may be advantageous, as is known in the art of immunology.

A peptide is typically formulated with a veterinarily acceptable carrier or diluent. Conventional formulations, carriers, adjuvants and diluents may be employed. These will of course be determined by the route of administration and purpose for which the peptide is being administered. Suitable carriers and diluents are known to those in the vaccine art, for example Freund's complete or incomplete adjuvant, aluminium hydroxide, saponin, DEAE-dextran, muramyl dipeptide, mineral oils, neutral oils (such as miglyol), vegetable oils (such as arachis oil), "Iscoms", liposomes, PLURONIC polyols or the Ribi adjuvant system (see, for example, GB-A-2189141). "PLURONIC" is a Registered Trade Mark. When the Th-epitope and B-cell epitope are presented as separate peptides in the same delivery vehicle, the peptides may be incorporated in liposomes.

A peptide of the invention may be linked to other antigens to provide a dual effect. For example, a peptide incorporating a GH sequence as the B-cell epitope may be linked to part or all of the somatostatin molecule to create, in addition to anti-GH antibodies, anti-somatostatin antibodies which would promote growth or it may be linked to part or all of a sex hormone molecule to provide for simulataneous immunocastration, or to part or all of luteinising hormone-releasing hormone.

The following Examples illustrate the invention. In the accompanying drawing:

FIG. 1 shows the results of a hypophysectomised rat experiment in which rats were treated with anti-peptide antibodies raised to a variety of peptides related to either bovine (b) or porcine (p) molecules. All were complexed with pGH prior to administration to the rats. The bars represent the standard deviation, with 6 animals per group.

EXAMPLE 1
Preparation of peptides

Peptides 238, 240 242 and 359 shown below were synthesised by the solid-phase method. More specifically, synthesis was carried out using an adaption of the Merrifield method (Merrifield, JACS, 85, 2149–2154, 1963) described by Houghten (Houghten, Proc. Natl. Acad. Sci. USA, 82, 5131–5135, 1985). Each peptide has an additional non-natural cysteine residue at its C-terminus.

| PEPTIDE | REFERENCE NUMBER |
|---|---|
| VPNLRGDLQVTASGVAETTNC (SEQ ID NO: 8) (FMDV 141–150 + VP3 Th-cell epitope + C) | 238 |
| VPNLRGDLQVLAQKVARTLPTASGVAETTN (SEQ ID NO: 9) (FMDV 141–160 + VP3 Th-cell epitope + C) | 240 |
| VPNLRGDLQVLAQKVARTLPTASGVAETT-NWFSKLASSAFC (SEQ ID NO: 10) (FMDV 141–160 + VP3 Th-cell epitope + additional residues) | 242 |
| TYIPEGQRYSIQNTQVAFTASGVAETTNC (SEQ ID NO: 11) (bGH 35–53 + VP3 Th-cell epitope + C) | 359 |

EXAMPLE 2
Test of peptide 240

Three groups of cattle of 5 animals per group were inoculated intramuscularly with 50 nM doses of a 141–160 FMDV peptide extended at the carboxy terminal by 17 additional natural residues plus a carboxy terminal non-natural cysteine residue (141–177+C) or by 17 additional residues from a "foreign" murine T-cell epitope plus a carboxy terminal non-natural cysteine residue (141–160+OVA+C) and peptide 240, respectively. The peptides were administered in incomplete Freunds adjuvant (FIA).

Neutralizing antibody responses were determined 28 days later. The sera were examined for virus neutralizing activity using a modification of the method described by Golding et al (Research in veterinary Science 20, 142–147, 1976). Briefly, 50 ul volumes of twofold dilutions of serum, prepared in Eagle's basal medium containing 2% cattle serum, were mixed with 50 ul of a suspension containing 100 TCID$_{50}$ of homologus FMD virus, adapted to grow in IB-RS-2 cells (di Castro, Arquivos do Instituto Biologico (Sao Paulo), 31, 63–78, 1964), in flat-bottomed microplates (Nunclon) and allowed to stand for 1 hr at room temperature.

Fifty ul of IB-RS-2 cells ($1\times10^6$ cells/ml) were then added to each well and the plates were sealed and incubated for 48 hr at 37° C. Finally, the plates were flooded with 10% citric acid in 0.85% saline to fix the cell sheets and inactivate remaining virus. The fixative was discarded after 30 min and the cells were stained by flooding the plates with 0.4% Naphthalene black in 0.85% saline. After a further 30 min the plates were rinsed in sterile distilled water, shaken free of droplets and allowed to dry by evaporation. Each test was-done in duplicate and the titration end-points were taken as the reciprocal of the serum dilution which gave confluent cell sheets in 50% of the wells expressed as a $\log_{10}$ value. The results are shown in Table 1 below.

TABLE 1

| Peptide | Animal Number | | | | |
|---|---|---|---|---|---|
| | 1 | 2 | 3 | 4 | 5 |
| 141–177 | <0.6 | <0.6 | <0.6 | <0.6 | <0.6 |
| 141–160 + OVA | <0.6 | <0.6 | <0.6 | <0.6 | <o.6 |
| 240 | <0.6 | 1.1 | 1.4 | 1.1 | <0.6 |

EXAMPLE 3
Test of peptide 359 General 1.4 mg of peptide 359 was introduced into pigs after dissolving in 140 ul of dimethyl formamide, dispersing in phosphate-buffered saline (PBS) and emulsifying in FIA. The peptide was administered subcutaneously at 4 sites in the neck region of large White piglets (5 weeks of age; approximately 9kg body weight) so as to give 500 ug peptide per pig. A second immunisation using a similar preparation was given 28 days later. On this occasion all were delivered in FIA. Blood samples were collected just prior to this immunisation and weekly thereafter, by vacuum-assisted venepuncture (Corvac, Sarstedt, U.K.) of the pulmonary vein. The sera were tested for antibody recognition of porcine growth hormone using an Enzyme Linked Immunosorbent Assay (ELISA) based on Voller, 1979 (Voller et al, The Enzyme Linked Immunosorbent Assay, Dynatech Europe, Guernsey) which was subsequently cross-linked by competition, in a similar assay, with aqueous hormone.

ELISA 96-well plates treated for immunoassay consistency (Nunc, Immuno-quality, High-binding capacity) were coated using 50 ug hormone/ml at 5 ug.well (100 ul) in sodium carbonate/bicarbonate buffer 0.05M pH 9.5 and allowed to stand overnight at +4° C. The hormone solution was carefully removed and the wells washed once with PBS. A solution of 3% haemoglobin was added to 'block' the wells and left overnight at +4° C. This was removed-and the wells washed three times with PBS to 0.05% Tween. All plates were allowed to dry slowly at room temperature and stored at −20° C. individually wrapped in cling-film. Sera under test were-added to each of the wells at 1/50th and subsequent $\log_{10}$ dilutions (100 ul) and left for 2 hours, at room temperature. This was removed and the wells washed three times in PBS, and replaced by 100 ul rabbit anti-pig IgG alkaline phosphate conjugate (Sigma) at $10^{-3}$ dilution. This was removed and washed as before. 100 ul of p-nitrophenyl phosphate at 1.0 mg/ml was added and the absorbance of the wells read using Titertek Multiscan Plus 2 with 405 nm filter.

Results

Table 2 shows that the presence of antibodies which recognised coated porcine growth hormone (and this would compete with aqueous hormone) could be detected in a number of pigs.

TABLE 2

Anti-pGH antibodies in peptide immunised pigs at 42 days, as measured by the ELISA technique

| Peptide | % Positive animals (n = 6) | |
|---|---|---|
| 359 | 1/50* | 1/500* |
|  | 100 | 100 |

*antisera dilution

EXAMPLE 4

Test of peptide 359 (biological assay of GH activity)

Immunoglobulin Preparations

Sera from larger blood samples taken from particular animals (indicated by the immunoassays) were fractionated by sodium sulphate precipitation (Johnstone & Thorpe, Immunochemistry in Practice, Blackwells, London, U.K., 1982) to isolate principally the gamma-globulins (IgG) which were extensively dialysed against PBS before being re-frozen at −20° C. Prior to use in animal experiments the purified IgG fractions were re-titrated to monitor the effects of precipitation, if any.

Hypophysectomised Rats

These animals are rendered pituitary (hypophysis) deficient by surgical removal. The assay monitors the overall effect of the hormone on body weight of the rat as well as the circulating levels of Somatomedin-C.

The surgery on male, Wistar rats was completed by Charles River U.K. Limited (Margate, Kent, U.K.) and delivered 14 days later at a weight range of 135–145 g. They were weighed and observed for a further 7–10 days, to ensure stable body weight and physical features (for example non-appearance of testicles) consistent with good health and complete surgery. Satisfactory animals were randomly allocated to provide six animals per treatment.

Procedure

Rats were injected daily with 0.5 ml PBS containing approximately 1 mg sheep IgG from the immunisation treatment under study (including negative controls), to which had been added 50 ug bovine or porcine growth hormone as appropriate. Before administration the hormone and IgG were mixed and allowed to stand at room temperature for 60 minutes. Injections were subcutaneous and intrascapular.

Animals were weighed and injected daily for 8 days, at the same time of day on each occasion. On the ninth day the animals were weighed, terminally anaesthetised and a blood sample taken from the aortic bifurcation. EDTA-plasma was frozen at −20° C. for subsequent estimation of relative total Somatomedin-C levels using materials supplied by Nichols Institute (San Juan Capistrano, Calif. 92675, USA).

Results

These are shown in FIG. 1. A variety of anti-peptide sera enhance the activity of bovine and porcine growth hormones when administered to these surgically modified rats. The best result, however, was obtained with anti-peptide 359 antibody (anti b35–53+T-cell epitope).

What is claimed is:

1. A peptide consisting of a sequence of up to 50 amino acids, said sequence including the sequence GVAE; and veterinarily acceptable salts thereof.

2. A peptide according to claim 1, which includes the sequence TASGVAETTN.

3. A peptide according to claim 1 further including a sequence capable of inducing an antibody response in a vertebrate which potentiates the activity of a growth hormone in said vertebrate.

4. A peptide according to claim 1 wherein the peptide consists of a sequence of up to 40 amino acids.

5. A peptide according to claim 1 wherein the peptide consists of a sequence of up to 30 amino acids.

6. A peptide according to claim 1 wherein the peptide consists of a sequence of up to 20 amino acids.

7. A peptide according to claim 1 wherein the peptide consists of a sequence of up to 10 amino acids.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Gly Val Ala Glu
  1

( 2 ) INFORMATION FOR SEQ ID NO:2:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Thr Ala Ser Gly Val Ala Glu Thr Thr Asn
1               5                   10

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Thr Tyr Ile Pro Glu Gly Gln Arg Tyr Ser Ile Gln Asn Thr Gln Val
1               5                   10                  15

Ala Phe Cys ( 2 ) INFORMATION FOR SEQ ID NO:4:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:4:

Tyr Ile Pro Lys Glu Gln Lys Tyr Ser Phe Leu Gln Asn Pro Gln Thr
1               5                   10                  15

Ser Leu Cys ( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Ala Tyr Ile Pro Glu Gly Gln Arg Tyr Ser Ile Gln Asn Ala Gln Ala
1               5                   10                  15

Ala Phe Cys ( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

```
Thr Tyr Ile Pro Glu Asp Gln Arg Tyr Thr Asn Lys Asn Ser Gln Ala
1               5                   10                  15

Ala Phe Cys
```

(2) INFORMATION FOR SEQ ID NO:7:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

```
Thr Leu Leu Pro Asp Glu Arg Arg Gln Leu Asn Lys Ile Phe Leu Leu
1               5                   10                  15

Asp Phe Cys
```

(2) INFORMATION FOR SEQ ID NO:8:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

```
Val Pro Asn Leu Arg Gly Asp Leu Gln Val Thr Ala Ser Gly Val Ala
1               5                   10                  15

Glu Thr Thr Asn Cys
                20
```

(2) INFORMATION FOR SEQ ID NO:9:

(i) SEQUENCE CHARACTERISTICS:
      (A) LENGTH: 31 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

```
Val Pro Asn Leu Arg Gly Asp Leu Gln Val Leu Ala Gln Lys Val Ala
1               5                   10                  15

Arg Thr Leu Pro Thr Ala Ser Gly Val Ala Glu Thr Thr Asn Cys
```

(2) INFORMATION FOR SEQ ID NO:10:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:10:

```
Val Pro Asn Leu Arg Gly Asp Leu Gln Val Leu Ala Gln Lys Val Ala
 1               5                  10                  15
Arg Thr Leu Pro Thr Ala Ser Gly Val Ala Glu Thr Thr Asn Gln Phe
             20                  25                  30
Ser Lys Leu Ala Ser Ser Ala Phe Cys
         35                  40
```

(2) INFORMATION FOR SEQ ID NO:11:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

```
Thr Tyr Ile Pro Gln Gly Gln Arg Tyr Ser Ile Gln Asn Thr Gln Val
 1               5                  10                  15
Ala Phe Thr Ala Ser Gly Val Ala Glu Thr Thr Asn Cys
             20                  25
```